United States Patent [19]

Steinbrecher

[11] 4,358,731

[45] Nov. 9, 1982

[54] APPARATUS AND METHOD FOR MOISTURE MEASUREMENT

[75] Inventor: Donald H. Steinbrecher, Woburn, Mass.

[73] Assignee: Philip Morris Incorporated, New York, N.Y.

[21] Appl. No.: 152,597

[22] Filed: May 23, 1980

[51] Int. Cl.³ ............................................. G01R 27/04
[52] U.S. Cl. ........................ 324/58.5 R; 324/58.5 A; 324/58.5 C
[58] Field of Search .................. 324/58.5 R, 58.5 C, 324/58.5 B, 58.5 A; 73/73

[56] References Cited

U.S. PATENT DOCUMENTS

| | | | |
|---|---|---|---|
| 2,548,598 | 4/1951 | Feiker, Jr. ....................... | 324/58.5 C |
| 2,671,884 | 3/1954 | Zaleski ........................... | 324/58.5 C |
| 4,104,585 | 8/1978 | Schofield ........................ | 324/58.5 C |
| 4,234,844 | 11/1980 | Yuki ............................... | 324/58.5 A |

FOREIGN PATENT DOCUMENTS 1111384  4/1968  United Kingdom .......... 324/58.5 C

Primary Examiner—Stanley T. Krawczewicz
Attorney, Agent, or Firm—Arthur I. Palmer; James E. Schardt

[57] ABSTRACT

A practice for moisture measurement wherein a transmission means is utilized in conjunction with a circuit means connected in shunt with the transmission means and adapted to receive a material to be tested such that the driving point impedance of the circuit means is dependent upon the moisture content of the material.

13 Claims, 2 Drawing Figures

FIG. I

APPARATUS AND METHOD FOR MOISTURE MEASUREMENT

BACKGROUND OF THE INVENTION

This invention relates to measurement techniques and, in particular, to measurement techniques for determining the moisture content of materials.

In the manufacture of a wide variety of products, it is often desired that the moisture content of the materials being processed be measured. In recent years, there has been an interest in utilizing electrical energy for making these measurements.

In some moisture measurement systems employing electrical energy, the energy is at microwave frequencies. U.S. Pat. No. 3,360,721 discloses one such microwave measurement system designed to detect the moisture content of tobacco. In this system, microwave energy at a level set by a variable attenuator is coupled to a microwave transmitter or horn. The transmitted energy passes through a tobacco sample holder to a microwave receiver also in the form of a horn. A precision variable attenuator follows the receiver and couples the received energy to a detector. The precision variable attenuator is set to provide a maximum detected signal in the absence of a tobacco sample in the holder. Subsequent introduction of a sample causes a reduction in detected signal which is then compensated for by a change in the setting of the precision variable attenuator. This change in setting equals the attenuation added to the system by absorbtion of the microwave energy by the tobacco sample and corresponds to the moisture content of the tobacco.

In another microwave system disclosed in British Specification No. 1,376,747, microwave energy from a source is split and coupled into two similar waveguides. Each waveguide includes two waveguide sections, one of which has an opening for receiving a cigarette rod. Ratios of the outputs of the waveguide sections are taken and these ratios used to determine the relative masses of tobacco and moisture in the tobacco rod. Another system in which a ratio of microwave energies is taken is that of U.S. Pat. No. 3,498,112 used for determining the moisture content of fuel oil. In this system, the energy from a microwave power source is again split, with one portion of the energy being coupled through an attenuator circuit and the other portion through a sample holder containing no sample. The attenuator circuit is set so that its output when compared in a ratio meter with the output energy from the empty sample holder gives a value of 1. Subsequent placement of an oil sample in the holder, provides a ratio reduction which can then be related to the oil moisture content.

U.S. Pat. No. 3,460,031 discloses a split waveguide moisture probe wherein the moisture content of a paper web is determined by passing the web through the gap between the probe sections. As in the system of U.S. Pat. No. 3,360,721, a variable attenuator at the waveguide output is used to determine the increased waveguide attenuation resulting from the passing paper web. This increased attenuation provides a measure of the web moisture content. This patent further discloses an alternate system for detecting web moisture using a split waveguide resonator probe. In this case, insertion of the web into the resonator gap changes the resonant frequency and Q of the resonator. These changes in these quantities can then be measured and utilized to determine web moisture content directly or as a cross-check against an attenuation measurement.

Other microwave systems utilizing an unbalanced condition in corresponding microwave waveguide sections are disclosed in U.S. Pat. No. 2,798,197 and British Specification No. 1,124,461. U.S. Pat. No. 2,798,197 discloses a microwave bridge circuit in which a sample is situated in one bridge arm and the other bridge arm is provided with a calibrated attenuator and phase shifter which are varied to obtain a balanced condition. The attenuator and phase shifter values are then used to determine the dielectric constant of the sample. In British Specification No. 1,124,461 two of the arms of a hybrid waveguide junction are brought into an unbalanced condition upon insertion in one of the arms of an oil sample whose water content is unknown and differs from that of a reference oil sample in the other arm. This unbalanced condition is measured and provides an indication of the unknown water content.

Other types of electrical energy moisture measurement techniques wherein the electrical energy is at frequencies lower than microwave frequencies have also been proposed. U.S. Pat. No. 3,795,984 discloses a system for measuring the moisture content of a fibrous material, such as, tobacco, by applying the output of a variable frequency oscillator to a tuned circuit having a measuring capacitor between whose plates pass the fibrous material. Such passage of the fibrous material causes a change in the electrical characteristics of the capacitor which result in a shift in the resonant frequency of the tuned circuit. This shift in resonant frequency is detected and used to vary the oscillator frequency until it resides at the new resonant frequency. At this frequency, the output of the tuned circuit reaches a voltage peak which is related to the energy absorbed by the measuring capacitor and, hence, to the moisture content of the fibrous material. This patent further teaches that the latter voltage is used to provide a measure of low moisture contents and that for high moisture contents such measure is derived from a signal representing the change in resonant frequency of the tuned circuit. U.S. Pat. No. 3,777,358 also discloses a system wherein the moisture content of a fibrous material is detected by measuring the peaks in output voltage of a tuned circuit having a measuring capacitor.

Another apparatus for measuring moisture content, this time of freshly prized remoistened tobacco in hogs heads, is taught in U.S. Pat. No. 3,766,471. In this apparatus, an oscillator signal is applied to a probe which is inserted in the tobacco and the component of the current of the probe circuit in phase with the oscillator signal determined. This current is a measure of the resistive component of the probe impedance and provides a measure of the tobacco moisture content.

While the many systems described above have provided some degree of success in moisture measurements, there still remains a need for a system having improved accuracy and reliability, particularly for measuring low levels of moisture content.

It is therefore a broad object of the present invention to provide an improved apparatus and method for moisture measurement.

It is a further object of the present invention to provide an improved apparatus and method for moisture measurement of tobacco.

SUMMARY OF THE INVENTION

In accordance with the principles of the present invention, the above and other objectives are realized in a measuring practice wherein a transmission means or line is shunted by a circuit means adapted to receive the material to be tested such that the driving point impedance of the circuit means is dependent upon the moisture content of the material. A variable oscillator feeds the transmission line and is controlled so that its frequency resides at a frequency at which the circuit means driving point impedance is at a minimum, thereby causing the circuit means to maximally inhibit energy transmission to the transmission line output. At this frequency, the energy available at the line output is thus at a minimum, this minimum being related to the driving point impedance of the circuit means and, therefore, to the received material moisture content. Detection of the line output thus provides a measure of the material moisture content.

Under the present practice, different moisture contents cause the circuit means to take on different driving point impedances which result in different frequencies at which the circuit means maximally inhibits energy transmission to the line output. These different frequencies are followed by the variable frequency oscillator, thereby maintaining the circuit means in condition to maximally inhibit energy transmission. Transmission line output is thus caused to take on different minimum values corresponding to the different driving point impedances and, therefore, to their different related moisture contents. These transmission line minima are detected in suitable detection apparatus to provide a measure of the different moisture contents.

In preferred form, detection of the transmission minima is carried out by correlating the minima to settings of a variable attenuator situated along the transmission line. The attenuator is initially set so that the line output is at a predetermined level with the oscillator set at a frequency at which the circuit means maximally inhibits energy transmission when in receipt of a reference material. During testing of a sample material, and subsequent to changing the oscillator frequency to the new frequency at which the circuit means maximally inhibits energy transmission, the attenuator is varied to adjust the line minimum to the predetermined level. The difference or variation in attenuator setting thus now correlates to the difference between the new minimum and the predetermined level and represents an attenuation value corresponding to the moisture content of the sample material relative to the moisture content of the reference material.

In further preferred form, the transmission line of the invention comprises a waveguide and the circuit means a waveguide cavity coupled to the waveguide side wall. In this form of the invention, the cavity is provided with an opening through which the material under test can be inserted into the field of the cavity to thereby effect changes in cavity driving point impedance.

BRIEF DESCRIPTION OF THE DRAWINGS

The above and other features and aspects of the present invention will become more apparant upon reading the following detailed description in conjunction with the accompanying drawings in which.

DETAILED DESCRIPTION

Figure 1:
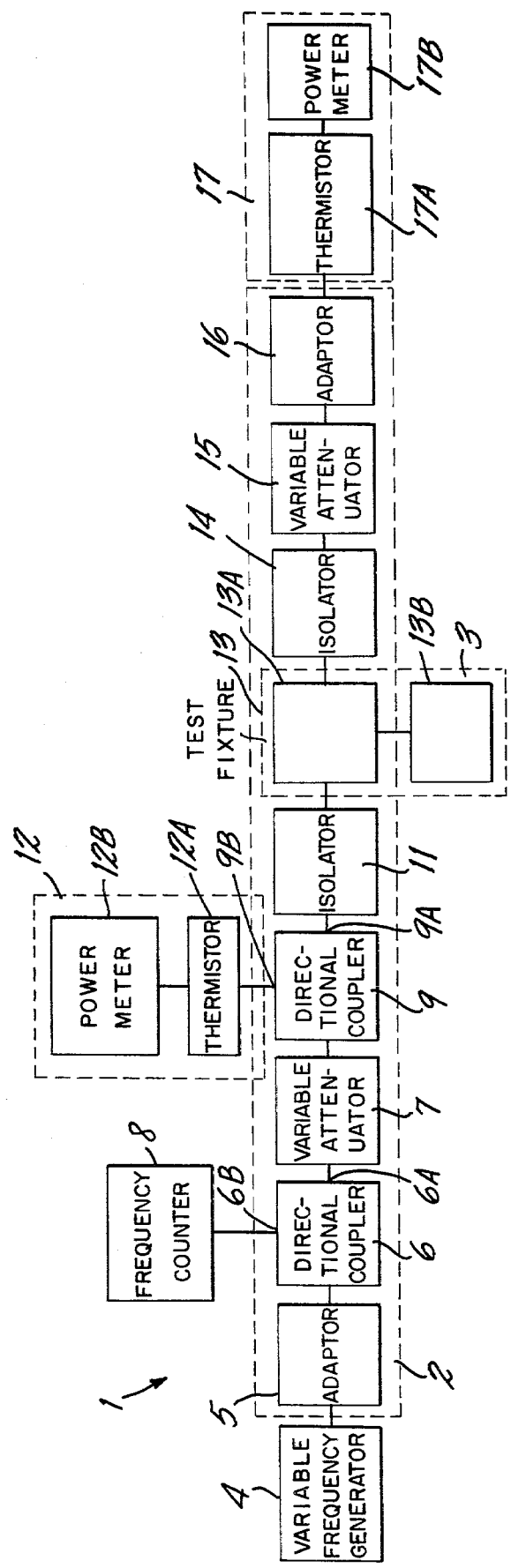
FIG. 1 shows, in block diagram form, the measuring apparatus embodying the practice of the present invention.

In FIG. 1, a moisture measuring apparatus 1 in accordance with the invention is illustrated in block diagram form. As shown, the apparatus 1 comprises components operable at microwave frequencies, although the principles of the invention are applicable to equivalent transmission lines and circuits operable at radio frequencies and other lower frequency ranges. The apparatus 1 comprises a main transmission line 2 and a circuit 3 connected in shunt with the line 2.

A variable frequency generator 4 such as, for example, a klystron, feeds the line 2 via an adaptor coupling 5. The adaptor 5 conveys the signal from generator 4 to a microwave directional coupler 6, having output ports 6A and 6B. The coupler 6 feeds a variable microwave attenuator 7 from its output port 6A and a frequency counter from its output port 6B.

A second directional coupler 9 having output ports 9A and 9B follows the attenuator 7 and directs energy from such output ports to an isolator 11 and a power detector 12, the latter comprising a thermistor 12A and a power meter 12B. The detector 12 monitors the input power to the test fixture 13 following isolator 11, this power being maintained at a predetermined level by the attenuator setting.

Test fixture 13 is adapted to receive the sample whose moisture is to be measured, and comprises first and second microwave sections 13A and 13B, the microwave section 13A forming a series segment of the line 2 and the microwave section 13B comprising a shunt cavity and forming the circuit 3. Following the section 13A of the fixture 13 is a further microwave isolator 14 coupled to a second variable attenuator 15. Attenuator 15 is connected to a further microwave adaptor 16 which is followed by a power detector 17. The detector 17 comprises a thermistor 17A and a power meter 17B and monitors the line 2 output power.

Figure 2:
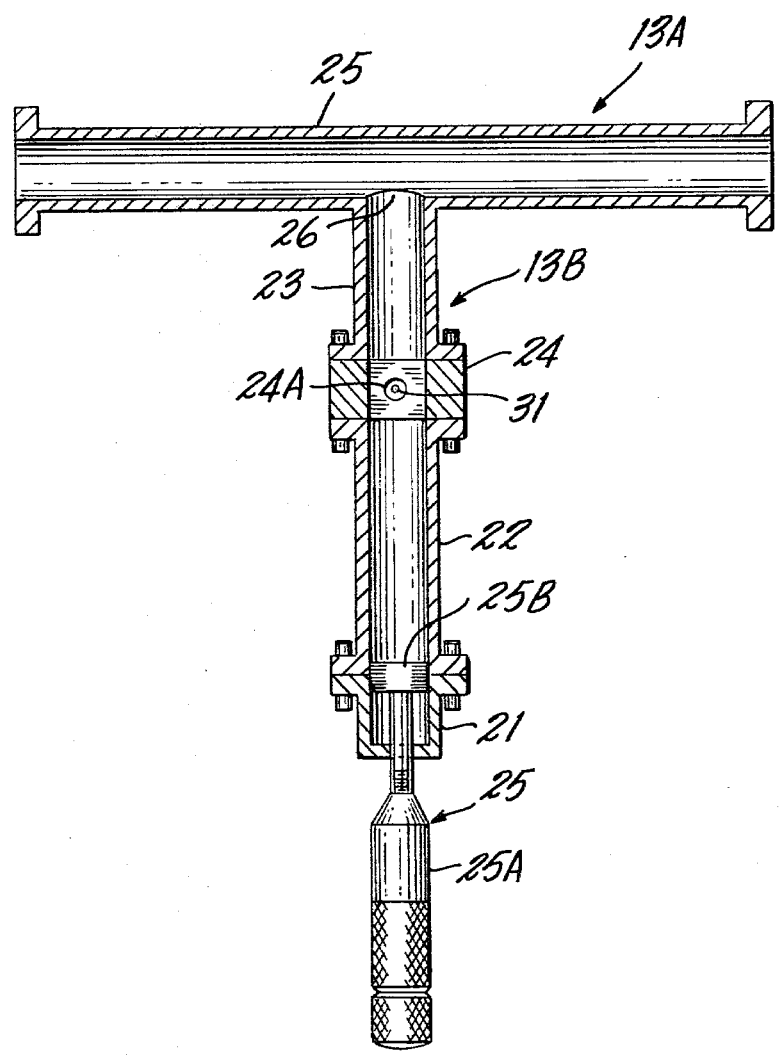
FIG. 2 illustrates in greater detail the test sample holder of the apparatus of FIG. 1.

In accordance with the invention, the shunt microwave section 13B is adapted to receive the sample under test such that its driving point impedance is dependent upon the moisture content of the sample. An illustrative embodiment of the shunt waveguide section 13B is shown in FIG. 2. Also shown in FIG. 2 is an illustrative embodiment of waveguide section 13A. As shown, the section 13B comprises lower, middle and upper waveguide segments 21, 22 and 23 which are suitably bolted together to form an integral structure. Between the middle and upper segments is further disposed a highly conductive metallic sample receiving element 24 (a typical material for element 24 might be aluminum) having an opening 24A extending therethrough and which, in the case shown, is a waveguide-beyond-cutoff aperture for supporting a tobacco rod 31 between opposing waveguide walls. Support of the rod 31 in this manner positions the rod at the point of maximum electric field and in the direction of the electric field vector of the shunt section, thereby ensuring maximum interaction of the field with the rod. Supported by the lower waveguide section is an adjustable short 25 having a rotatable vertically moveable control rod 25A for positioning a shorting plate 25B along the length of the shunt section for tuning purposes, as will be discussed hereinbelow.

The waveguide section 13A comprises a waveguide segment 25 having an aperture 26 in its sidewall for coupling to the upper segment 23 of the shunt section 13B. As shown, the latter segment is formed integrally with the segment 25 in T configuration.

With the waveguide sections 13A and 13B having the form shown in FIG. 2, the remaining components of the line 2 will be of compatible waveguide construction. Conventional waveguide devices can typically be utilized for these components.

The effect of the shunt microwave section 13B on the power being coupled through the transmission line 2 is to reflect certain of the power and thereby inhibit this power from reaching the line 2 output which is being monitored by the detector 17. With the variable frequency generator 4 supplying energy at a frequency $f_r$ at which the shunt section driving point impedance is at a minimum, the shunt section reflects a maximum amount of power. The power reaching the line 2 output will thus be at a minimum related to the driving point impedance.

As above-described, the driving point impedance of the shunt section 13B depends upon the moisture content of the sample received by the section. Thus, different samples with different moisture contents will result in different driving point impedances and, therefore, different degrees of maximum reflection at the minima of the different impedances. Different minima corresponding to the different impedance minima and representative of the different moisture contents will thus appear at the line 2 output for the different samples, thereby providing a detectable measure of the different moisture contents.

In basic operation, a sample is applied to the shunt section 13B so as to alter its driving point impedance as above-described. In the shunt section of FIG. 2, this is brought about by inserting the rod 31 through the apertures 24, thereby situating the rod in the region of maximum electric field. With the sample so disposed, the frequency of the oscillator 4 is varied until it is at a frequency at which the driving point impedance of the shunt section is at a minimum value. This is accomplished by varying the frequency of the oscillator until the power output from the line 2, as monitored by the detector 17, is at a minimum indicating maximum energy reflection and thus a minimum impedance of the shunt section. This minimum output power is related to the minimum impedance value and thus provides a measure of the moisture content of the sample under test. Determination of the moisture content of subsequent samples is carried out by repeating the above procedure.

The minimum power readings derived from the apparatus 1 can be converted to percent moisture or oven volatile (OV) readings by a suitable chart correlating respective minimum power outputs to OV. The latter, in turn, can be prepared by utilizing two similar samples and determining the minimum power output for one sample with the apparatus 1 and the OV reading for the other sample using a conventional oven heating technique. This will provide a correlation of one minimum power output and a particular OV. Repeating the process for samples of different OV will enable generation of a complete conversion chart. In this regard, the detector 17 in a similar manner can itself be calibrated in OV, so as to permit directly reading OV from the meter without the necessity of a separate chart.

While the above operating procedure of the measuring apparatus 1 provides satisfactory moisture content determinations, a preferred method of operating the apparatus makes use of the precision variable attenuator 15. In this operation, at the frequency of minimum driving point impedance, the attenuation of the attenuator 15 is changed so as to maintain the output power of the line 2 substantially constant. The change in attenuator attenuation setting thus correlates to the attenuation of the shunt section and thereby provides an accurate measure of same, and, hence, sample moisture content. In accordance with this operation, a reference material is first applied to the shunt section. With the reference material applied, the oscillator frequency is varied until the shunt section driving point impedance is at a minimum resulting in a minimum output power. Attenuator 15 is then adjusted to provide a predetermined output power level at the detector 17, and the reference material is thereafter removed. At this point, the apparatus 1 is in condition to provide moisture content measurements. The sample to be tested is applied to the shunt section. Again the frequency of the oscillator is adjusted to the frequency of minimum driving point impedance by monitoring when the output power at the detector 17 is at a minimum. The attenuator 15 is then varied until the output power of the line 2 at the detector 17 is again at the predetermined level. The variation in attenuator setting now corresponds to the shunt section attenuation, and therefore provides a measure of the sample moisture content relative to the reference moisture content. Again under this procedure, a chart relating changes in attenuator attenuation settings to OV can be made so as to convert attenuator readings into more conventional OV readings, the chart being made in a analogous manner to that discussed above.

The shunt section 13B might be of a construction for which the material of the sample under test and the supporting structure for the sample result in a shunt section driving point impedance for which the frequency of minimum impedance is beyond the variation range of oscillator 4. In such case, means is provided in the section for varying the driving point impedance so that it has a minimum at a frequency within the variation range of the oscillator 4. In practice, this is accomplished by positioning the plate 24B so that it substantially cancels the parallel admittance represented by the tobacco sample and the supporting apertures at a frequency within the oscillator range.

During operation of the apparatus 1, other minor adjustments might also have to be made to ensure optimum accuracy. Thus, for example, the attenuator 7 might have to be varied to maintain constant input power to the holder 13.

Utilization of the apparatus 1 has been found to provide moisture content readings which are unaffected by material density and are of high accuracy, comparable to that obtained using conventional oven heating techniques, particularly, for measurement of low moisture content levels. This high accuracy results from the utilization of the shunt section 13B which increases significantly the sensitivity of the apparatus 1, since small changes in material moisture content are evidenced as relatively large changes in the value of minimum shunt section driving point impedance and, therefore, minimum output power.

Tests have been conducted with the apparatus 1 on a large number of tobacco samples ranging in density from 0.2 gm/CC to 0.3 gm/CC and ranging in OV from 3 OV to 16 OV and an accuracy in moisture content measurement of at least ±0.296 OV obtained. In conducting these tests, the following equipment for the apparatus 1 components was employed.

| Component | Manufacturer Equipment |
| --- | --- |
| frequency generator 4 | HP8620C and HP86250B |
| adaptors 5 and 16 | HPX281A |
| directional couplers 6 and 9 | HP752C |
| variable attenuators | HP382A |
| isolators | Microlab/FXR X157A |
| power meters 12B and 17B | HP435A |
| thermistor 1 | HP8481A |
| thermistor 2 | HP8484A |
| frequency counter 8 | EIP35kC |

The sample holder for these tests was as shown in FIG. 2, the guide segment 25 having dimensions of 0.45 inches by 0.90 inches and the guide segments 21–23 having the same dimensions. The adjustable short was an HP X923A and the apparatus was operated at a frequency of 9.1 GHz using the $TE_{10}$ mode.

It should be noted that adjustment of the frequency generator 4 and the variable attenuators 7 and 15 in accordance with practice under the invention can be carried out automatically by conventional control circuitry. Thus, control circuits monitoring the power meters 12B and 17B can be utilized to effect control over the attenuator 7, attenuator 15 and generator 4. Suitable control circuits for performing these functions might, for example, use an IEEE 488 bus to perform measurements under computer control.

In all cases, it is understood that the above-described arrangements are merely illustrative of the many possible specific embodiments which represent applications of the present invention. Numerous and varied other arrangements can readily be devised in accordance with the principles of the present invention without departing from the spirit and scope of the invention.

What is claimed is:

1. Apparatus for use in determining the moisture content of a material comprising:
   transmission means;
   circuit means connected in shunt with said transmission means and adapted to receive said material such that the driving point impedance of said circuit means is dependent on the moisture content of said material,
   a variable frequency oscillator connected to the input of said transmission means;
   means for adjusting said oscillator so that it generates energy at a frequency equal to a frequency at which said driving point impedance is at a minimum;
   and means for monitoring the output of said transmission means.

2. Apparatus in accordance with claim 1 further comprising:
   means for varying said circuit means such that said driving point impedance has a minimum within the frequency range of said oscillator.

3. Apparatus in accordance with claim 2 wherein:
   said circuit varying means cancels the shunt admittance represented by said material and the receiving means thereof when said material is received by said circuit means.

4. Apparatus in accordance with claim 1 wherein:
   said adjusting means is responsive to the output of said transmission means and adjusts said frequency to a frequency at which said output is a minimum.

5. Apparatus in accordance with claim 4 further comprising:
   variable attenuator means connected in series with said transmission means.

6. Apparatus in accordance with claim 5 further comprising:
   means responsive to the output of said transmission means for varying said attenuator means so as to maintain said output at a predetermined level after said frequency of said oscillator has been adjusted to a frequency at which said output is a minimum.

7. Apparatus in accordance with claim 1 or 6 wherein:
   said circuit means comprises a microwave cavity.

8. Apparatus in accordance with claim 7 wherein:
   said transmission means comprises a length of microwave waveguide;
   and said cavity is coupled to a side wall of said waveguide.

9. Apparatus in accordance with claim 8 wherein:
   a common aperture couples said waveguide and said cavity.

10. Apparatus in accordance with claim 8 wherein:
    said material is tobacco in cigarette rod forms;
    and said cavity includes means for supporting said cigarette rod between opposing sidewalls.

11. Apparatus in accordance with claim 10 wherein:
    said supporting means has a waveguide-beyond-cutoff aperture through which said cigarette rod extends.

12. Apparatus in accordance with claim 10 further comprising:
    adjustable short means positioned in said cavity to cancel the parallel admittance of said first and second apertures and said tobacco content of said rod.

13. A method of measuring the moisture content of a material comprising:
    providing a transmission means;
    providing a circuit means in shunt with said transmission means;
    applying energy to said transmission means at a frequency at which said driving point impedance is at a minimum;
    monitoring the output level of said transmission means;
    applying said material to said circuit means such that the driving point impedance of said circuit means is dependent on the moisture content of said material;
    varying the frequency of said energy until said driving point impedance is returned to said minimum; and
    varying the attenuation of said transmission means subsequent to applying said material to restore the output of said transmission means to said monitored level, the attenuation variation being proportioned to and therefore indicative of the moisture content of said material.

* * * * *